United States Patent [19]

Schroeder

[11] Patent Number: 4,726,359
[45] Date of Patent: Feb. 23, 1988

[54] PROTECTIVE END CAPS ON ROLLED CONDOMS

[76] Inventor: Peter Schroeder, 3125 #C, Fairview Ave. East, Seattle, Wash. 98102

[21] Appl. No.: 747,246

[22] Filed: Jun. 21, 1985

[51] Int. Cl.⁴ .............................................. A61F 5/00
[52] U.S. Cl. ................................. 128/79; 128/132 R; 604/347
[58] Field of Search ..................... 128/79, 157, 132 R; 604/346, 347, 349, 289, 170, 171; 206/306, 69; 2/168

[56] References Cited

U.S. PATENT DOCUMENTS

| | | | |
|---|---|---|---|
| 2,326,159 | 8/1943 | Mendel | 128/157 |
| 2,448,938 | 9/1948 | Wayne | 128/79 |
| 2,577,345 | 12/1951 | McEwen | 128/79 |
| 3,301,394 | 1/1967 | Baermann et al. | 206/306 |
| 3,469,685 | 9/1969 | Baermann | 206/306 |
| 4,281,648 | 8/1981 | Rogers | 128/79 |

FOREIGN PATENT DOCUMENTS 326719  3/1930  United Kingdom ................ 604/349

Primary Examiner—Gene Mancene
Assistant Examiner—Cary E. Stone
Attorney, Agent, or Firm—Anthony D. Cipollone

[57] ABSTRACT

The present invention relates to protective end caps on rolled condoms.

These protective end caps are designed to attach to rolled condoms to indicate the orientation, direction of unrolling, of the condoms. These protective end caps are then separated from the condoms after the unrolling of the condoms and placement on the male organ insuring that the outer surface of the condoms remains sterile and uncontaminated while it is being placed on the male organ.

2 Claims, 4 Drawing Figures

PROTECTIVE END CAPS ON ROLLED CONDOMS

BACKGROUND OF THE INVENTION

1. Field of the Invention

The instant invention relates to end caps used as protective coverings on rolled condoms, their use as contraceptive devices, to overcome the inherent problems of sterility and contamination on rolled condoms without such protective coverings.

The original uses of condoms had the twofold purpose of preventing conception and transmission of veeral diseases by preventing direct contact of the genital organs of the partners during sexual intercourse.

The tremendous increase in both the incidence and types of sexually transmitted disease that is now due to contact with genital fluids and secretions rather than skin contact has given rebirth to the use of condoms as the only means currently available as a reasonable solution to the problem.

However, the use of condoms to guard against the new strains and types of sexually transmitted diseases requires added sophistication in the design and use of condoms so that the problem is alleviated rather than aggravated.

Misuse of condoms severely limits their utility in this respect. This misuse may be largely eliminated by the instant invention of adding the end caps to the rolled condom.

The end caps of this invention eliminate the problem of orientation of the condom in rolling and unrolling a rolled condom prior to use. The more obvious problem in determining the orientation of the rolled condom prior to use is the disruption in the continuity of the ambiance which may be present prior to sexual intercourse if there develops a quest for "roll direction" during these intense moments of mutual concentration between or among the partners as the case may be.

But an even more serious side effect of this problem of orientation is the possibility of contamination of the surface of the tip of the condom. During a reversal of its rolling direction those preseminal fluids and secretions may be left on the outer surface of the condom which comes into direct contact with the partner. 2. Description of Prior Art The prior art in this field is scant.

U.S. Pat. No. 2,904,041 by A. L. Brown discloses a protective shield for an external body member and more particularly to a combined mechanical and chemical prophylactic or similar device. This invention deals with a shield, or sheath, chemical and prophylactic as a single sealed system.

U.S. Pat. No. 3,363,624 by Sam Fisherman relates to a medicated prophylactic device with a desensitizing agent within the device for a body member inserted therein.

U.S. Pat. No. 4,143,423 by Jack J. Sternlict as far as the subject invention is concerned introduces a coated condom.

U.S. Pat. No. 4,446,860 describes medication receptacles added to mechanical birth control devices such as condoms used to release various non-contraceptive creams, jellies, foams, etc., to expose the genital organs to the medication.

OBJECT AND SUMMARY OF THE INVENTION

It is the object of this invention to incorporate distinguishable removable end caps on the distal or closed end of rolled condoms that will indicate the orientation of the condom, that is, the direction of unrolling.

These end caps will be over the outside tubular portion of the condom and extend from the distal or closed end of the condoms either completely or partially up the tubular portion of the condoms.

These end caps will be made of a latex, fabric, sponge, textile, or some distinctive suitable polymer such that it will impart a surface feel which is distinguishable from the smooth rubber-like feel inside the condom which is to be placed on the head of the penis and unrolled over the shaft.

In addition, these end caps will have the foregoing properties so that they may function as the embodiment of this invention.

The end caps shall have such flexibility that they will cover the rolled condoms on their outside face, that is, the outside portion of the condoms that will have no contact with the male genitals.

The end caps will be made of suitable composition such that they will be easily differentiated by surface feel from the rolled condoms smooth-like inside surface as described above and will indicate to the user the orientation so that the rolled condoms will be unrolled with the end caps surface on the outside when the condom is placed over the male genital.

These end caps will remain in place until the condoms are partially or fully in position at which time the end caps are removed.

The end caps will also be made of a material such that they are impermeable to preseminal fluids.

The end caps will also be made such that they are separable from the condom at that point in time when the condom is partially or fully in position. This separability is the key to the protective properties and the nature of this invention.

The differentiated surface feel of the end cap compared with the smooth slippery feel of the condom itself will allow the user to determine the orientation for unravel by feel alone, eliminating the problem of the direction of unravel.

The impermeability of the end cap to preseminal fluids and the differentiated surface feel will prevent any such fluids from collecting on the outside of the unrolled condom and further protect the outside surface from contamination.

The end caps not only will be impermeable but will also be minimally or non-absorbent to those lubricating and protective agents placed on the outside of the condom itself.

Since the end cap is separable from the condom and its outer surface, when the condom is ready for use after implantation on the penis, it will have no contamination and sterility will be intact because the end caps themselves will be removed at this point.

The end caps are such that they are not firmly removed until the condom is placed upon the head of the penis and have been partially rolled down along the penis shaft past the point where the end cap has been incorporated into the rolled portion. The preferred embodiment of the invention is for the end caps to simply fall away on their own if the material from which the end caps are made has no adhesiveness to the condom itself.

Other embodiments of the invention envision adhesive-backed end caps which must be peeled off prior to entry.

While the self removing end caps have the advantage that the user need not take active steps to remove the end cap, the second method has the advantage that the condom itself can be completely unrolled over the penis and made ready before the end cap is removed and that the adhesive backed end cap may be made smaller with resulting cost savings.

BRIEF DESCRIPTION OF THE DRAWING

FIG. 3 also shows various other configurations and sizes (B, C, D) of the instant invention, the end caps (numerals 2', 2'', 2''') and the fully unrolled condom (numerals 4', 4'', 4''') just prior to removal of the end cap.

DESCRIPTION OF THE INVENTION

Figure 1:
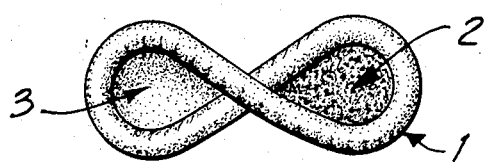
FIG. 1 shows a typical rolled condom prior to unravelling in an orientation showing the rolled portion of the condom, (numeral 1); the instant invention, the end cap (numeral 2); the inside smooth portion of the condom (numeral 3) which surface has direct contact with the male penis.
Figure 2:
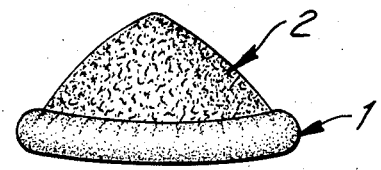
FIG. 2 is a view of a typical rolled condom as it appears when initially placed on the penis wherein the rolled smooth inner portion of the condom (numeral 1) is shown and the end cap on the distal side or closed side is shown (numeral 2).

An end cap (2) is incorporated onto a condom (4) prior to rolling the condom for packaging. The condom (4) is then rolled to the configuration as in FIG. 1 with the end cap (2) over the outside surface as in FIG. 2.

The inner surface of the end cap (2) which make contact with outer surface of the condom (4) must be impermeable, chemically inert, non-adhesive, non-clinging and have minimal or non-absorbency of the chemical lubricants used on and with the condom itself.

The inner surface of the entire end cap may be a coating formed of any suitable material. The preferred embodiment is a rubber or plastic substance or polymer which will not be affected by the chemicals on and composing the outer surface of the condom itself, which is impermeable to preseminal fluids and flexible so that the end cap may be rolled with the condom. The materials readily available for the formation of the inside surface of the end cap (2) having these necessary properties will include several types of materials but should not be limited to the following examples:

1. Plastic Materials
   (A) PVC
   (B) Polyethylene
   (C) Acetate
   (D) Polypropylene
   (E) Etc.
2. Metallic Foils
   (A) Tin
   (B) Aluminum
   (C) Etc.
3. Elastomers
   (A) Latex
   (B) Butyl rubber
   (C) EPDM
   (D) Etc.

The exposed or outer surface of the end cap (2) may be of the same composition as its inner surface or a different material such that this exposed surface has a distinctly differentiated feel from the smooth interior of the condom.

Examples of materials usable on the exterior portion of the end cap (2) include fabric (woven and unwoven), flocking, sponge and foam. Also suitable are plastic and elastomeric materials which have been either treated or marked with ridges and furrows to eliminate a smooth surface and highlight the feel differentiation required.

Composite materials which may be used for the end cap (2) would combine two materials. Examples: slot, PVC, texturized rubber, foamed plastic with aluminum foil backing, etc.

A single material may also be used provided it would incorporate the features required of both the contact surface with the condom and the exposed surfaces of the end cap (2). Examples of this include foamed polyethylene, close cell sponge rubber, a higher denser latex relative to the condom latex with a roughened exposed surface to indicate differentiation of feel.

Another embodiment of the invention may have the inner surface of the end cap (2) attached to the exterior surface of the condom (4) by use of suitable adhesives which have the same properties of the inner surface of the end cap in that the adhesive used is impermeable with minimal absorbency to preseminal fluids and lubricants used on or incorporated on the condoms, chemical inertness and non-reactivity with the material and lubricants of the exterior portion of the condoms, flexibility to be rolled with the condom, and having mechanical and chemical properties permitting facile separation between the outer surface of the condom (4) and the inner surface of the end cap (2).

Figure 3:
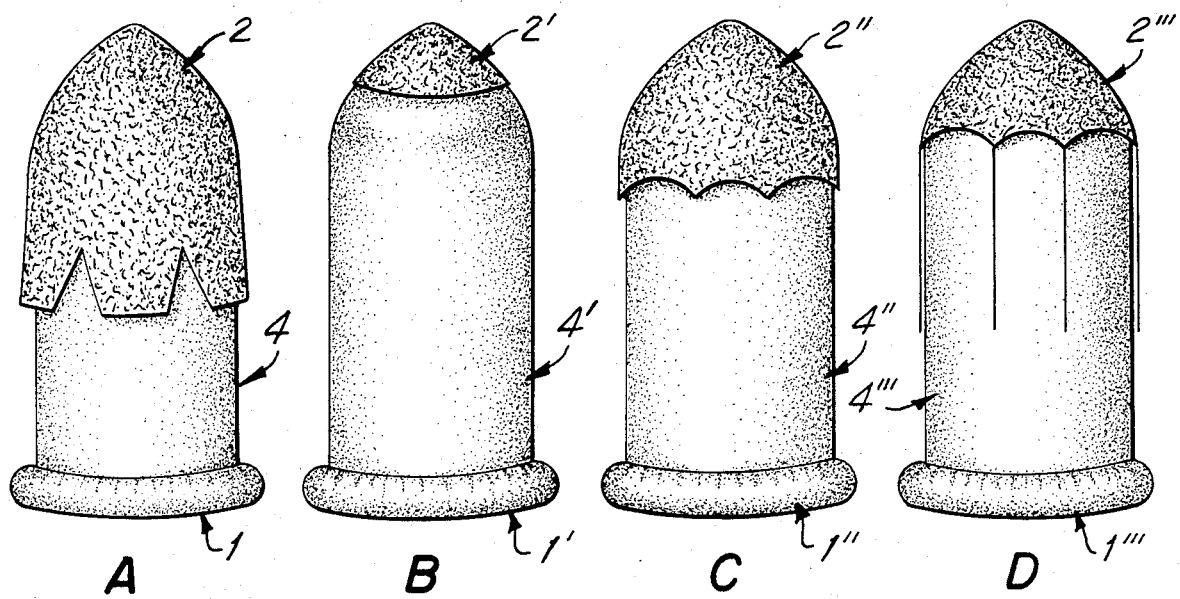
FIG. 3 shows a typical rolled condom partially unrolled on penis shown as configuration A with the as yet unrolled portion of the condom on (numeral 1); the outside tubular portion over the penis and not covered by the end cap (numeral 4); the end cap (numeral 2).
Figure 4:
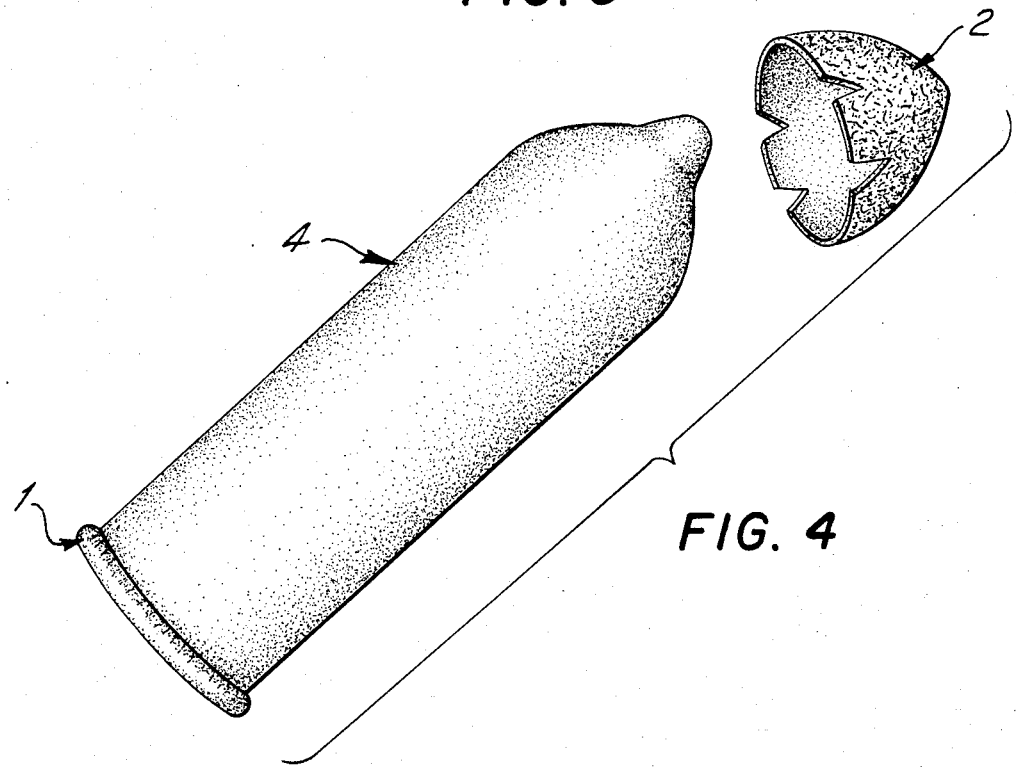
FIG. 4 shows a fully unrolled condom as it would be over the male genital with the unrolled portion (numeral 1); the now fully extended outer tubular portion (numeral 4); and the now separated end cap (numeral 2) just prior to final use.

Once the user has removed the condom (4) with the end cap (2) from its package and discarded the packaging, he would feel the both sides of the rolled condom. Provided suitable instructions have been supplied with the packaging, the indication would be that the smooth slippery side is the condom itself (1) which he then places on the head of the penis as in FIG. 2. The roughened side distinguished by its non-slippery or different feel is the end cap (2) at the distal or closed end of the condom (4). The end cap (2) would be simply unrolled once properly positioned as with any other condom over the penis. Once unrolled passed the position where the end cap is attached, as in FIG. 3 or FIG. 4, depending on the style of end cap used either configuration A, B, C, or D, the end cap would fall away or be removed as in FIG. 4. At this point, the condom is ready for use, and the heretofore problems associated with just plain condoms would be resolved.

If the user should inadvertantly put the wrong surface on his penis, that is the end cap outer surface, he would reverse it and unroll it in the proper position and even though the end cap has made contact with the preseminal fluids and is contaminated, this end cap is discarded prior to use, so that the partners can be certain that there has been no contamination of the condom while it was being put over the penis.

The end cap (2) therefore serves the useful purpose of keeping the condom sterile and uncontaminated prior to use and further because of its surface differentiation allows facile unrolling of the condom in its proper orientation so that the flow of energy and ambiance of the moment is not lost and there is not disturbing nuisance.

What is claimed is

1. An end cap for a condom which has a smooth outer and inner surface comprising an interior contact surface in contact with the outer surface of the condom and an exterior surface which has a differentiated feel and touch from the inner surface of the rolled condom to indicate orientation of unrolling and which may be rolled with the condom without damaging the condom or end cap where in the interior contact surface of the end caps has the following properties: impermeability with minimal or non-absorbency to preseminal fluids and lubricants used on or incorporated in the condoms, chemical inertness and non-reactivity with the material and lubricants of the outer surface of the condom, flexibility to be rolled with the condom, facile separation from the outer surface of the condom once the condom has been fully unrolled, such properties causing the end cap to be held on the condom when the condom is rolled.

2. The end cap in claim 1 wherein the interior surface of the end cap is attached to the outer surface of the condom by an adhesive having the following properties: impermeability with minimal or non-absorbency to preseminal fluids and lubricants used on or incorporated in the condoms, chemical inertness and non-reactivity with the materials and lubricants of the exterior portion of the condoms, flexibility to be rolled with the condoms and having mechanical and chemical properties permitting facile separation between the outer surface of the condom and the interior surface of the end cap, such properties causing the end cap to be held on the condom when the condom is rolled.

* * * * *